(12) United States Patent
Reimoser et al.

(10) Patent No.: US 6,894,300 B2
(45) Date of Patent: May 17, 2005

(54) ION BEAM FACILITY

(75) Inventors: Stefan Reimoser, Dresden (DE); Michael Solbrig, Munich (DE)

(73) Assignee: Siemens Aktiengesellschaft, München (DE)

( * ) Notice: Subject to any disclaimer, the term of this patent is extended or adjusted under 35 U.S.C. 154(b) by 146 days.

(21) Appl. No.: 10/371,892

(22) Filed: Feb. 21, 2003

(65) Prior Publication Data

US 2004/0118081 A1 Jun. 24, 2004

(30) Foreign Application Priority Data

Dec. 20, 2002 (DE) ......................................... 102 61 099

(51) Int. Cl.⁷ ............................. A61N 5/10; H01J 33/00
(52) U.S. Cl. ............................. 250/505.1; 250/517.1; 250/492.3; 250/423 R
(58) Field of Search ........................... 250/505.1, 517.1, 250/492.3, 423 R

(56) References Cited

U.S. PATENT DOCUMENTS

| | | | |
|---|---|---|---|
| 4,870,287 A | 9/1989 | Cole et al. | |
| 5,585,642 A | 12/1996 | Britton et al. | |
| 2004/0069958 A1 * | 4/2004 | Dahl ....................... | 250/492.3 |
| 2004/0183033 A1 * | 9/2004 | Moriyama et al. ....... | 250/492.3 |

FOREIGN PATENT DOCUMENTS

| DE | OS 100 10 523 | 9/2001 |
|---|---|---|
| EP | 0 986 070 | 3/2000 |
| EP | 0 986 071 | 3/2000 |

OTHER PUBLICATIONS

"The High–Energy beam–Transport System for HIMAC," Mizota et al., Mitsubishi Electric Advance, vol. 62 (1995) pp. 2–4.

"An H light Ion Synchrotron for Radiation Therapy," Arduini et al. Nuclear Instruments and Methods in Physics Research A 365 (1995) pp. 542–552.

"Design of a Centre for Biologically Optimised Light Ion Therapy on Stockholm," Brahme et al., Nuclear Instruments and Methods in Physics Research B 184 (2001) pp. 569–588.

"Cancer Therapy with Particle Accelerators," Amaldi, Nuclear Physics A654 (1999) pp. 375c–399c.

"Tumortherapie mit Ionenstrahlen," Spektrum der Wissenschaft, vol. 1 (1999), pp. 42–51.

"Engineering Design and Study of the Beam Position Accuracy in the "Riesenrad" Ion Gantry," Reimoser et al.

* cited by examiner

Primary Examiner—Nikita Wells
(74) Attorney, Agent, or Firm—Schiff Hardin LLP

(57) ABSTRACT

An ion beam facility has a first ion beam system for a first ion type that contains a first ion beam generator and a first ion transport line with at least one first ion switch for one of at least two first irradiation stations and has a second ion beam system for a second ion species with a second ion transport line or is fashioned expandable therewith. At least one of the first irradiation stations also can be operated with the second ion type or the ion transport lines are arranged proceeding essentially parallel to one another. For the expansion, the first ion transport line is conducted along a wall of a building of the ion beam facility and the wall is prepared for openings, so that at least one of the first irradiation stations also can be operated with the second ion type via the subsequently installable, second ion transport line at the other side of the wall, or space is reserved behind the wall for at least the second, subsequently installable ion transport line.

61 Claims, 7 Drawing Sheets

ION BEAM FACILITY

BACKGROUND OF THE INVENTION

1. Field of the Invention

The present invention is directed to an ion beam facility.

2. Description of the Prior Art

The article by U. Linz, "Tumortherapie mit Ionstrahlen", Spektrum der Wissenschaft, Dossier 1/1999, pages 42 through 51, for example, discloses that fast protons or other charged particles release their energy in more concentrated form than X-ray quanta of gamma rays, for example in the human or animal body. As a result thereof, they are especially suited for combating tumors. Correctly controlled, they mainly damage the tumor, whereas the surrounding, healthy tissue is unaffected. This yields significant advantages such as less serious side effects, faster healing and fewer late complications. Approximately twenty therapy centers, which are listed in the article, are known worldwide for the aforementioned tumor therapy.

For an ion beam facility wherein a number of irradiation sites or stations proceed fan-like from an ion beam generator, further, at least portions of the appertaining floor plan are disclosed by German OS 100 10 523.

SUMMARY OF THE INVENTION

An object of the present invention is to provide an improved ion beam facility that, among other things, enables expansions and remodeling with optimally short interruptions in the operations of the ion beam facility.

The above object is achieved in an ion beam facility according to the invention having a first ion beam system for a first ion type, having at least two first irradiation stations, a first ion beam generator, a first ion transport line, and at least one first ion beam switch in the first ion transport line for one of the first irradiation stations. The first ion transport line is conducted along a wall of a building of the ion beam facility, and the wall is prepared for subsequently making openings therein, so that at least one of the first irradiation stations can also be operated by a second ion beam system for a second ion type, that will have a second ion transport line subsequently installed at an opposite side of the wall from the first ion transport line.

The above object also is achieved in accordance with the invention in an ion beam facility having a first ion beam system for a first ion type, having at least two first irradiation stations, a first ion beam generator, a first ion transport line, and at least one first ion beam switch in the first ion transport line for one of the first irradiation stations. In this ion beam facility as well, the first ion transport line is conducted along a wall of a building of the ion beam facility. Space for at least one subsequently installable second ion transport line, of a subsequently installed second ion beam system for a second ion type, is reserved on the opposite side of the wall from the first ion beam transport line.

As a result of the wall being prepared for openings, particularly given implementation of the wall as a radiation-blocking wall, an expansion of the ion beam facility from, for example, a first ion beam system for hydrogen atoms, to add a second ion beam system, for example for carbon ions is facilitated. The expansion work can be initially carried out without interrupting the operations of the first ion beam system and, following the expansion, irradiation stations of the first ion beam system can be easily and quickly re-equipped for a mixed operation in the framework of both ion beam systems or for exclusive operation with the second ion beam system because of the openings already provided in the wall. Since the second ion beam system for the heavier ion type also can be operated with the first ion type with appropriate readjustments, an alternating operation with the one or the other ion types can ensue exclusively with second ion beam system. The aforementioned readjustments are implemented with each change. In one embodiment, the ion beam generator and the ion transport line of the first ion beam system can even be entirely foregone as a result, but of course, the advantage of operations continuing with the second or the first ion beam system given maintenance of the first or the second ion beam system is lost, compared to a mixed operation with both ion beam systems. The aforementioned advantages can likewise be achieved in the inventive ion beam system, wherein an ion transport line of the first ion beam system is conducted along a wall of a building of the ion beam facility and space is reserved behind the wall for at least one subsequently installable second ion transport line of the second ion beam systems.

For also equipping an ion beam facility at the outset for later operation with heavier ions, it is in theory possible to replace the components of the first ion beam system by the significantly larger components of the second ion beam system. As a result, however, the initial investment would be disadvantageously burdened due to the necessity of over-dimensioning spaces reserved for later use, and the replacement of the components, moreover, would disadvantageously lead to long down times of the ion beam facility. Fashioning the components to be "over-dimensioned" from the outset for later operation with heavier ions as well would, in fact, prevent the aforementioned, long down times but would additionally disadvantageously burden the initial investment due to the expensive, "over-dimensioned" components in addition to the large spaces. These disadvantages are avoided in the inventive systems described above so that the investment for the first ion beam system and its construction is burdened neither by excessively large spaces nor "over-dimensioned" components of the ion beam system.

The aforementioned advantages also can be achieved in an inventive ion beam facility, wherein at least one of the first irradiation stations of the first ion beam system also can be operated at the second ion beam system, as well as in an inventive ion beam facility, wherein the two ion transport lines of the first and second ion beam system are separately conducted through a wall in parallel. The parallel structure also produces a compact overall structure of the ion beam facility.

DESCRIPTION OF THE PREFERRED EMBODIMENTS

Figure 1:
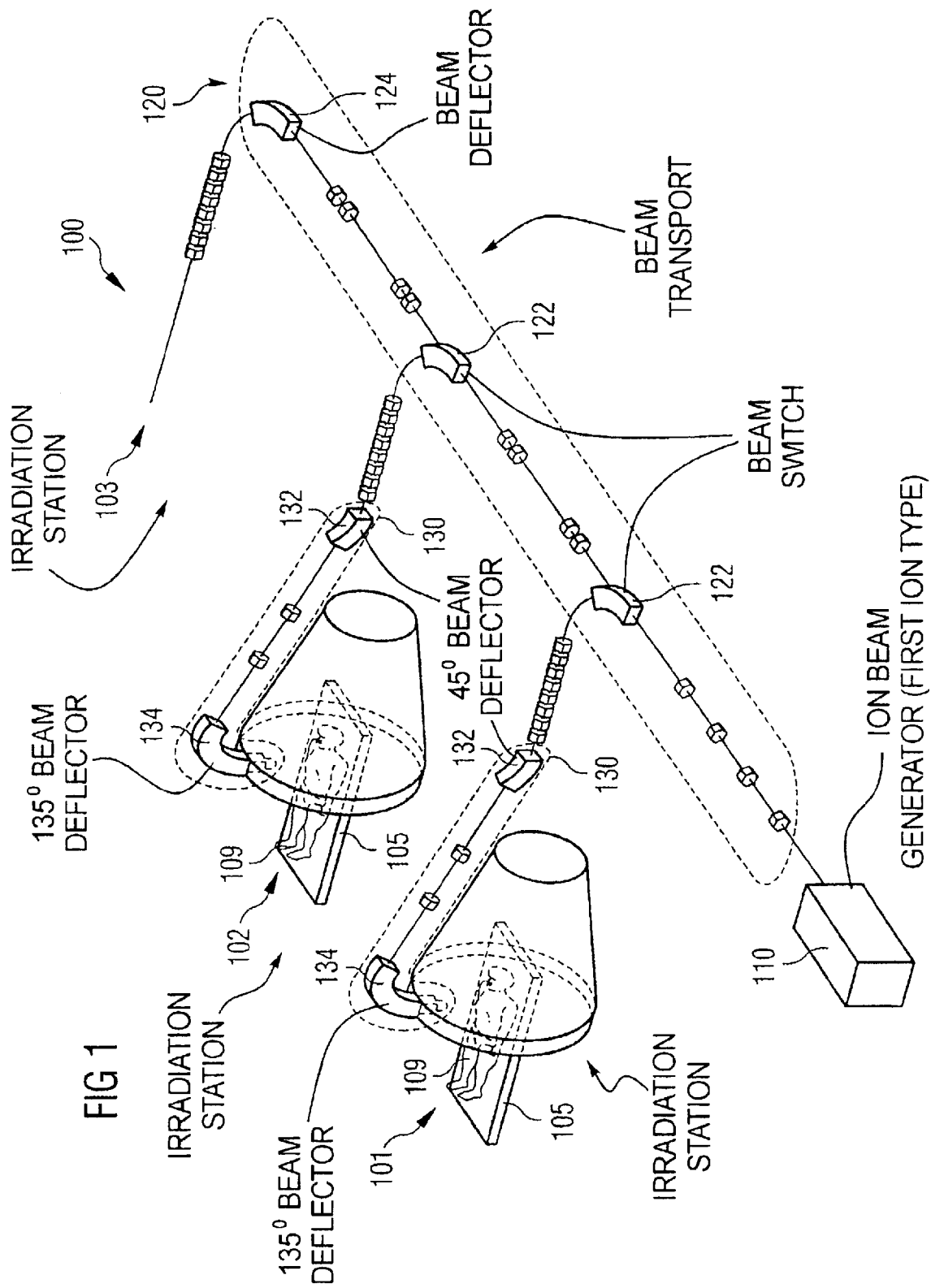
FIG. 1 shows a first ion beam system in accordance with the invention in a perspective view.

As a component part of an ion beam facility serving as an exemplary embodiment of the invention, FIG. 1 shows a first ion beam system 100 for the irradiation of patients 109 with ions of a first ion type, particularly with protons, which are also referred to as hydrogen ions. The first ion beam system 100 has an ion beam generator 110 with an ion source and an ion accelerator that is connected to an ion transport line 120. The high-energy ions are conducted via the ion transport line 120 to respective patients 109 at the selectable irradiation stations 101, 102 and 103. To that end, the ion transport line 120 contains two ion beam switches 122 and an ion beam deflector 124. Each of the ion beam switches 122 is characterized by two switching states. In a first switching state, the ion beam coming from the ion beam generator is deflected in the direction of one of the irradiation stations 101 or 102, and, in a second switching state, the ion beam passes through the ion beam switch 122 on a straight line.

The irradiation station 103 is fashioned such that the ion beam emerges rigidly prescribed in the horizontal direction. The two other irradiation stations 101 and 102 each has an ion beam guidance mechanism 130 that is rotatable around a horizontal axis that accepts the ion beam in the direction of the axis, transports it away from the axis and aligns it at a right angle to the axis, intersecting the axis. Among other things, the ion beam guidance mechanism 130 has a 45° ion beam deflector 132 and a 135° ion beam deflector. The intersection of the ion beam with the axis represents the isocenter of a target region in one of the patients 109, who is placed on a patient support mechanism 105 in a prescribable direction. By rotating the beam guidance mechanism 130, it steers the ion beam through the isocenter from different angles during the irradiation of one of the patients 109.

In the ion beam system 100, conventional components corresponding to well-known transport, acceleration and focusing techniques for ions are employed, in combination, matched to one another and set such that the desired acceleration and injection parameters are achieved.

Figure 2:
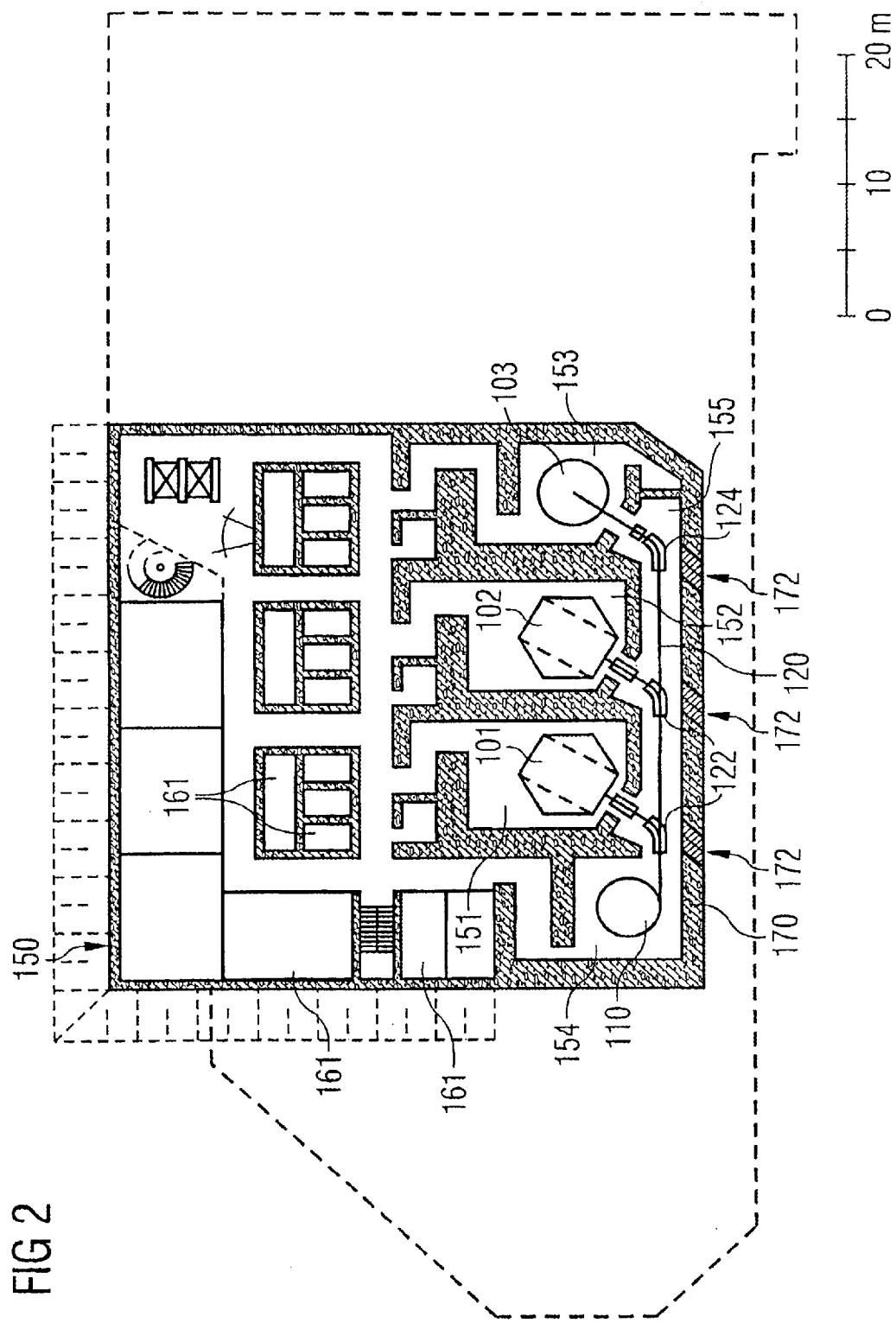
FIG. 2 is a floor plan of the ion beam facility of FIG. 1 in a first stage of expansion.
Figure 3:
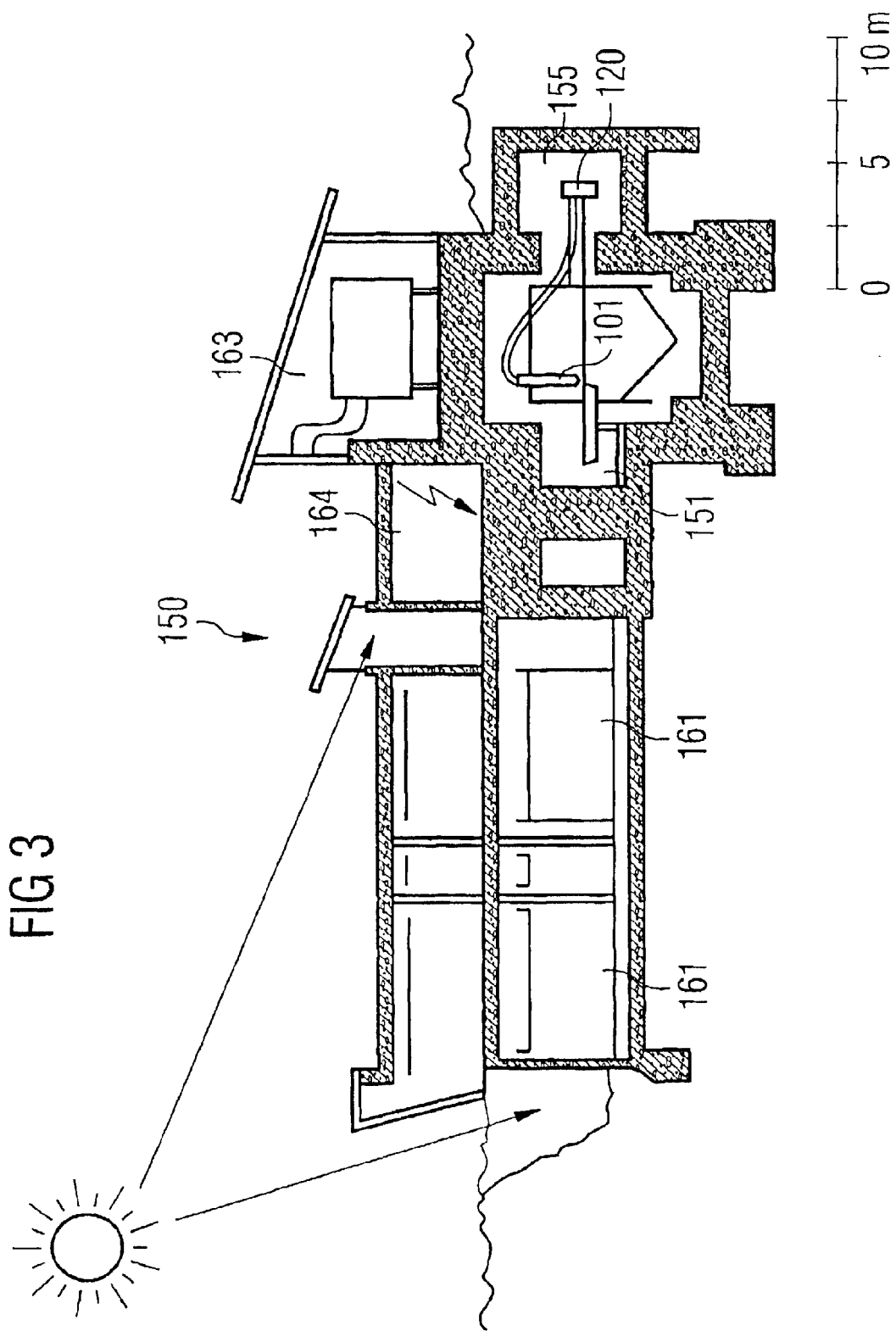
FIG. 3 is a cross-section through the ion beam facility of FIG. 2 in a first embodiment.
Figure 4:
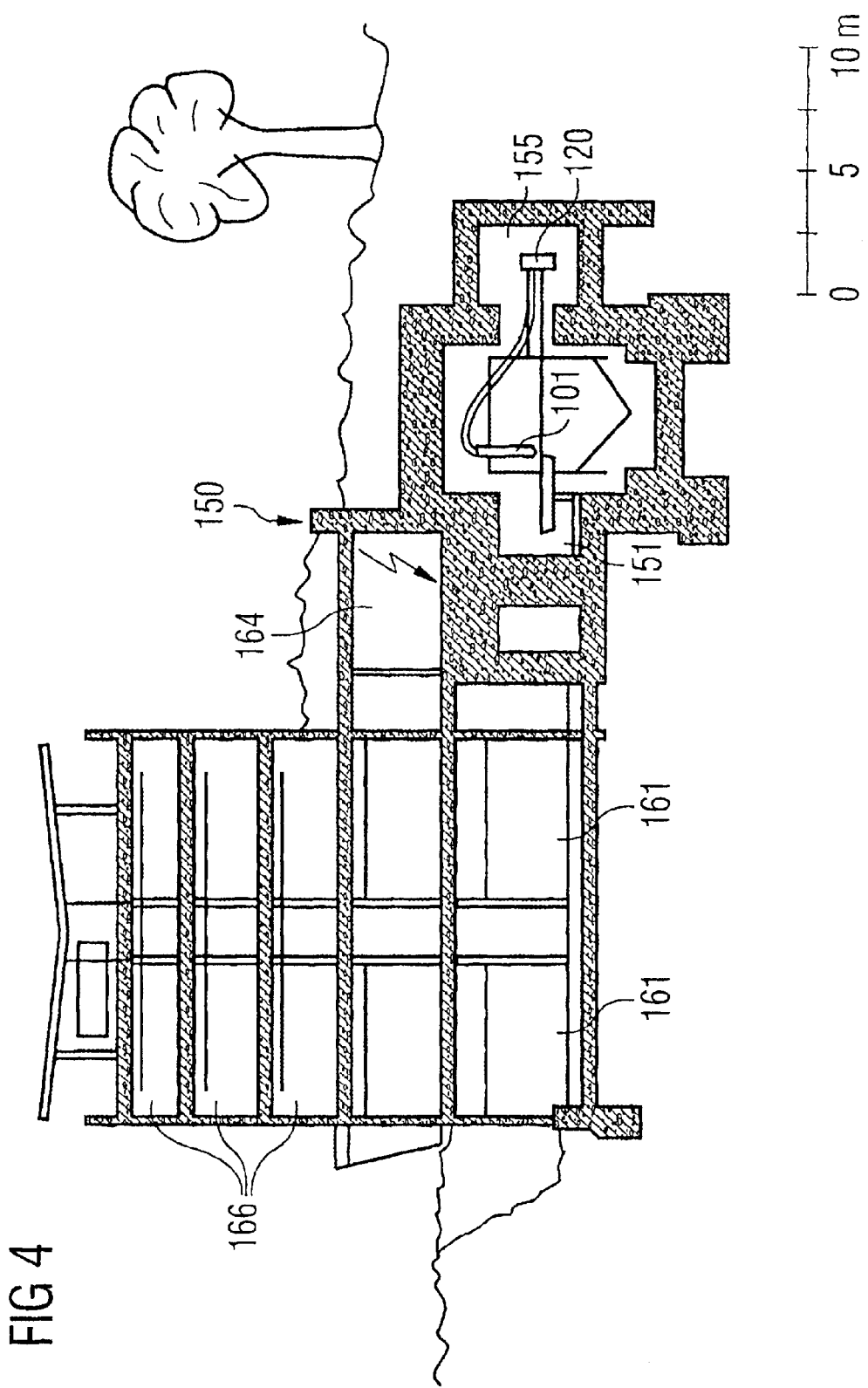
FIG. 4 is a cross-section through the ion beam facility of FIG. 2 in a second embodiment.

As an exemplary embodiment of the invention, FIG. 2 shows the ion beam facility in a first expansion stage. The ion beam system 100 of FIG. 1 is arranged in a building 150, the floor plan of which is outlined in FIG. 2. The ion beam line 120 is thereby conducted along a radiation-blocking wall 170 of the building 150 that simultaneously represents an outside wall of the building 150 in the first expansion stage. The irradiation stations 101, 102 and 103, the ion beam generator 110 and the ion transport line 120 are accommodated in rooms 151 through 155 of the building 150 that are shielded from one another in terms of radiation. The radiation blocking is thereby assured by means of concrete walls a few meters thick. The radiation blocking is necessary since ionizing secondary radiation arises given the interaction of the ion beam with matter, for example with air or tissue devices for measuring radiation parameters in the ion beam generator 110 and/or the ion beam transport line 120, etc. The ionizing secondary radiation contains mainly fast neutrons, which have energy sufficient to damage human cells. For protecting personnel and the public from this radiation, the rooms 151 through 155 are insulated by concrete walls or by the adjoining ground, as shown in FIGS. 3 and 4. Dependent on, among other things, the ion type, the radiation blocking must be dimensioned in thickness such that the radiation level on the far side of the blocking is lowered to an acceptable level as prescribed by law. Further rooms 161 of the building 150 are available for monitoring the operation of the facility, for treating and caring for patients, as well as for office activities connected therewith.

In its first expansion stage, the ion beam facility is already designed and configured such that, without interrupting the operation of the ion beam system 100, it can be expanded by a second ion beam system 200 for a second ion type that is characterized by heavier ions than the first ion species, for example carbon ions. The floor plan for a building expansion shown with a broken line is reserved for this expansion. Further, the wall 170 is already configured for openings 172 so that, during the course of the expansion, at least some of the individual irradiation stations 101, 102 and 103 can be redesigned for operation only with the second ion beam system 200, or for a mixed operation with both ion beam systems 100 and 200, with little time expenditure, and thus without significant operating interruptions. For the openings 172, the wall 170 can be provided, for example, with suitable wall facings or scorings or panels. Until an expansion of the ion beam facility, the openings 172 are tightly closed with corresponding closures that have properties corresponding to those of the wall 170 in terms of radiation attenuation. Further details about the aforementioned expansion are described below with reference to FIG. 5.

FIG. 3 shows a cross-section through the ion beam facility shown as a floor plan in FIG. 2. The cross-section is conducted roughly through the rooms 155 and 151. The building 150 is designed such that at least the radiation-blocked rooms 151 through 155 have the upper edge of their ceilings coinciding roughly to the surface of the ground, so that the ground is additionally used as radiation protection, thereby achieving an optimally good and simple, additional radiation protection. For example, a room 163 for electrical operating equipment as well as a room 164 for air-conditioning equipment, particularly for the rooms 151 through 155, are provided in a further story above the rooms 151 through 161.

FIG. 4 shows another cross-section through the ion beam facility of FIG. 2. Compared to FIG. 3, additional stories, for example for further hospital-oriented functions, include the room 166 and a special room 164 for air-conditioning equipment is provided.

Figure 5:
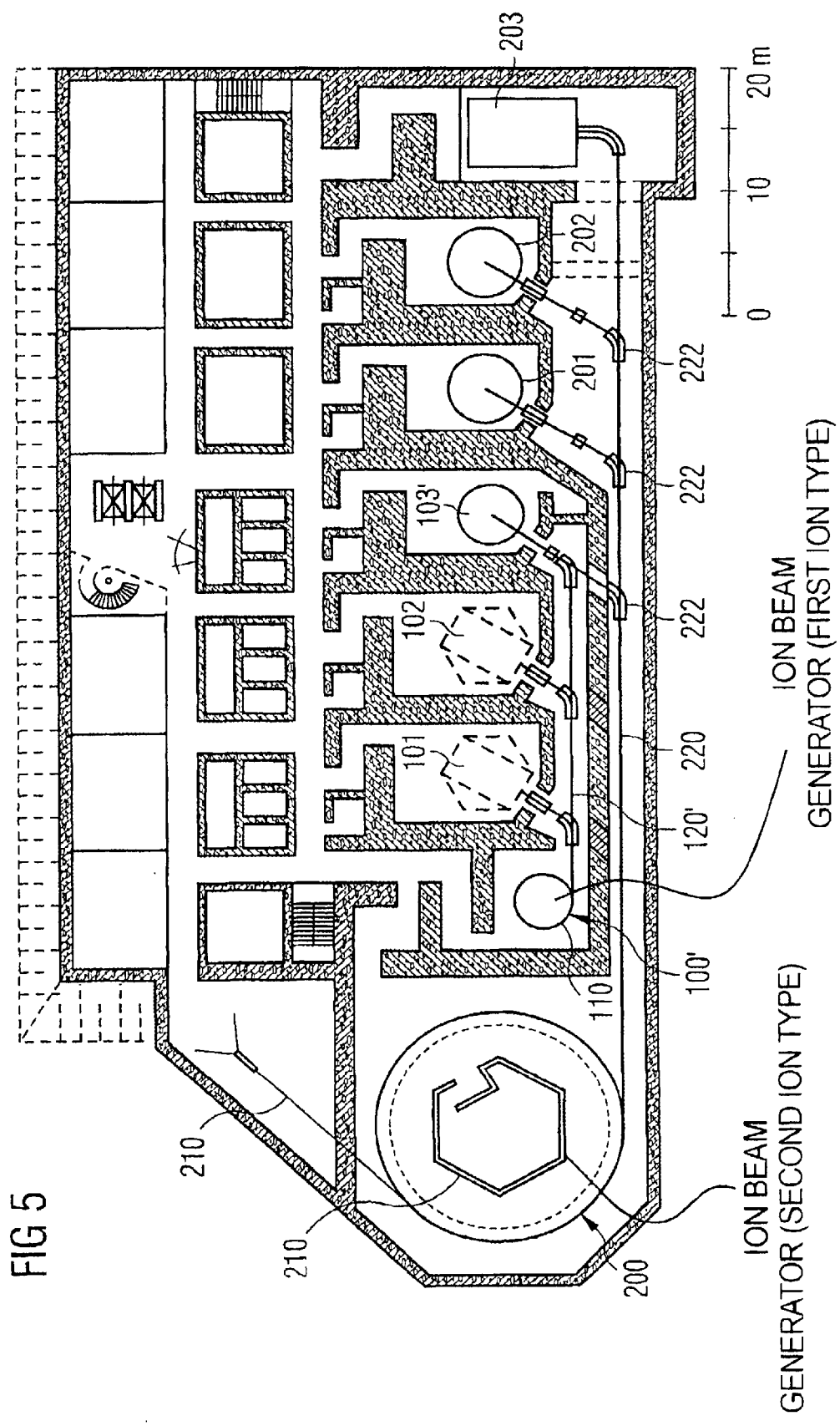
FIG. 5 is a floor plan of the ion beam facility of FIG. 2 expanded by a second ion beam system in a first embodiment.

Proceeding on the basis of FIG. 2, FIG. 5 shows the ion beam facility after expansion by the second ion beam system 200. Similar to the first ion beam system 100, the second ion beam system 200 has an ion beam generator 210, an ion transport line 220 with corresponding ion beam switches 222 and three irradiation stations 201, 202 and 203. The irradiation stations 201 and 202 have a rigidly prescribed, horizontal ion beam discharge, in contrast which the irradiation station 203 is fashioned according to the irradiation station described in the article by S. Reimoser et al., "Engineering design and study of beam position accuracy in the "Riesenrad" ion gantry", Nuclear Instruments and Methods in Physics Research A 456 (2001), pages 390 through 410. In particular, the ion beam generator 210 and a rotatable ion beam guidance mechanism for the irradiation station 203 as well are thereby significantly bulkier than the comparable components for the first, lighter weight ions due to the possibility of operating with the heavier ions, so that particularly the rooms for the ion beam generator 210 and the irradiation station occupy considerably more space than for the first ion beam system.

The ion beam line 220 is conducted along the wall 170. This has the advantage that the irradiation stations 103, 102 and/or 101 of the first ion beam system 100 are simple to re-equip for mixed operation with both ion beam systems 100 and 200 or an operation only with the second ion beam system 200. Only the irradiation station 103, or first the irradiation station 103 and then the irradiation station 102, or first the irradiation station 103, and then the irradiation station 103 and finally the irradiation station 101, are refitted for a simple re-equipping and short down times in the use of the irradiation stations 103, 102 and/or 101. Among other things, the ion transport line 220 is suitably configured for the expansion by using ion beam switches 222. The openings 172 provided in the wall are then uncovered as needed for the refitting and the irradiation stations 103, 102 and/or 101 as well as the ion transport line 120 are then suitably remodeled or adapted for the re-equipping. In particular, the radiation attenuation of the rooms 153, 152 and/or 151 must be upgraded for operation with the heavier ions by, for example, the walls being reinforced with pre-fabricated parts in the form of concrete blocks. Since the second ion beam system 200 is decoupled from the first ion beam system 100 in terms of radiation, the expansion and remodeling of the ion beam facility can be largely implemented given continued operation of the first ion beam system 100. It is also advantageous that the investment for the first ion beam system 100 and its building 150 initially incurs no additional costs for enlarged rooms, as would be the case if, instead of the described expansion, replacement of the components of the first ion beam system 100 by components of the second ion beam system occurred. Moreover, such replacement would disadvantageously involve very long down times of the ion beam facility.

As an example, the irradiation station 103' is refitted for the mixed operation in FIG. 5 proceeding from the irradiation station 103. To that end, the ion transport line 220 has an ion beam-switch 222 at an appropriate location. Proceeding from the ion transport line 120, further, the ion transport line 120' is correspondingly adapted in the right end region as a component of an adapted, first ion beam system 100'. Compared to the room 153 for the irradiation station 103, finally, the room for the radiation station 103' is redesigned by, for example, thickening the walls for the radiation protection. The irradiation station 103' thereby exhibits the particular advantage that, given maintenance of the adapted, first ion beam system 100' or of the second ion beam system 200, operations can continue with the second ion beam system 200 or the adapted, first ion beam system 100', whereas, given maintenance of the adapted, first ion beam system 100', readjustments of the second ion beam system 200 enable it to also be operated with ions of the first ion type.

Figure 6:
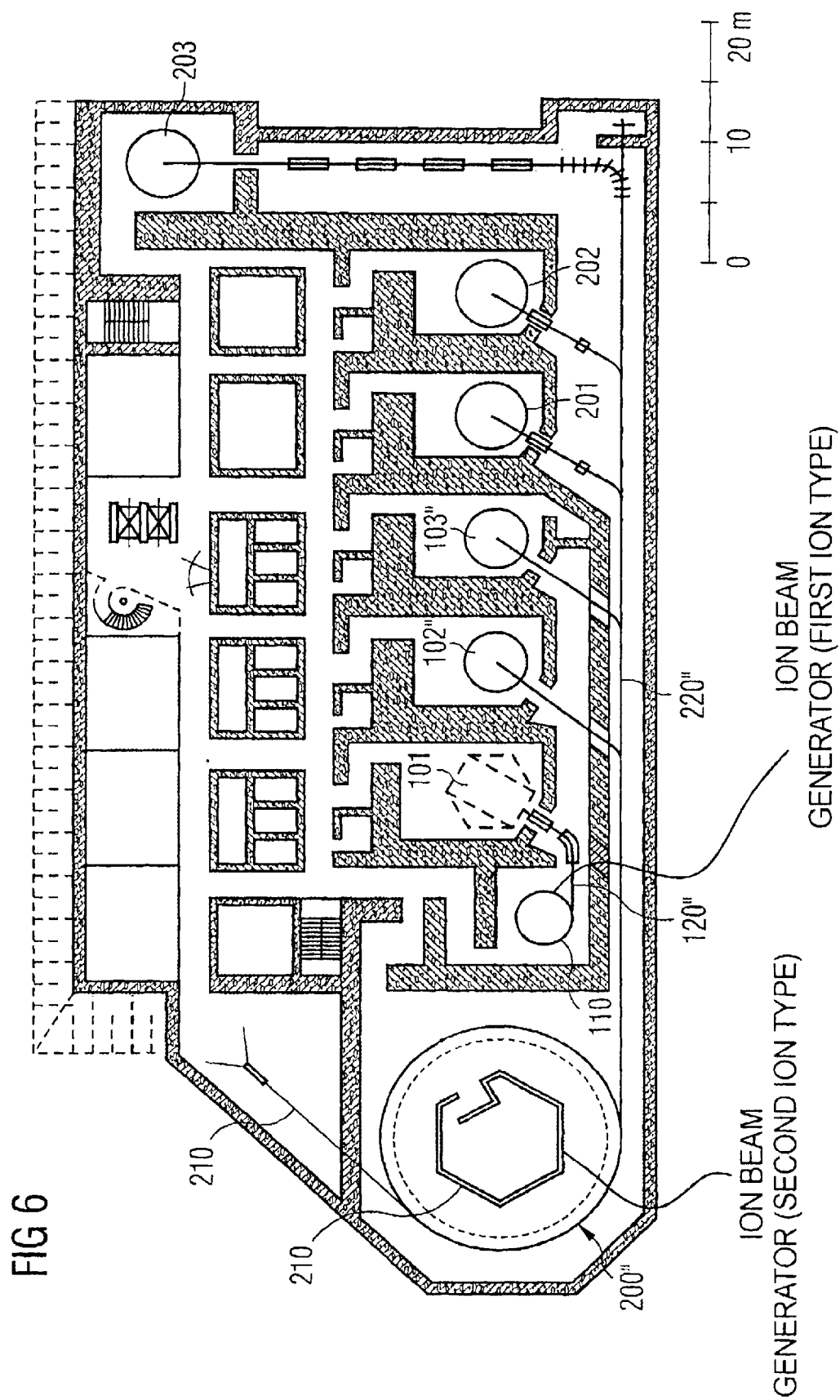
FIG. 6 is a floor plan of the ion beam facility of FIG. 2 expanded by a second ion beam system in a second embodiment.

As a further exemplary embodiment of the invention, FIG. 6 shows another version for expansion. Compared to FIG. 5, the embodiment of FIG. 6 does not enable mixed operation. Proceeding from FIG. 2, the irradiation stations 102 and 103 have been refitted into irradiation stations 102" and 103" with a rigidly prescribed beam exit angle that can only be operated with a second ion beam system 200". The ion transport line 120 is remodeled into the shortened ion transport line 120' for exclusive supply of the irradiation station 101. The irradiation stations 102", 103", 201, 202 and 203" are connected to an ion transport line 220" of the ion beam system 200". That part of the ion transport line that proceeds vertically in FIG. 6 and immediately precedes the irradiation station 203" is thereby designed such that the ion beam emerges from above at an angle of 600 at the irradiation station 203" with respect to a patient support surface that is parallel to the floor of the room.

Figure 7:
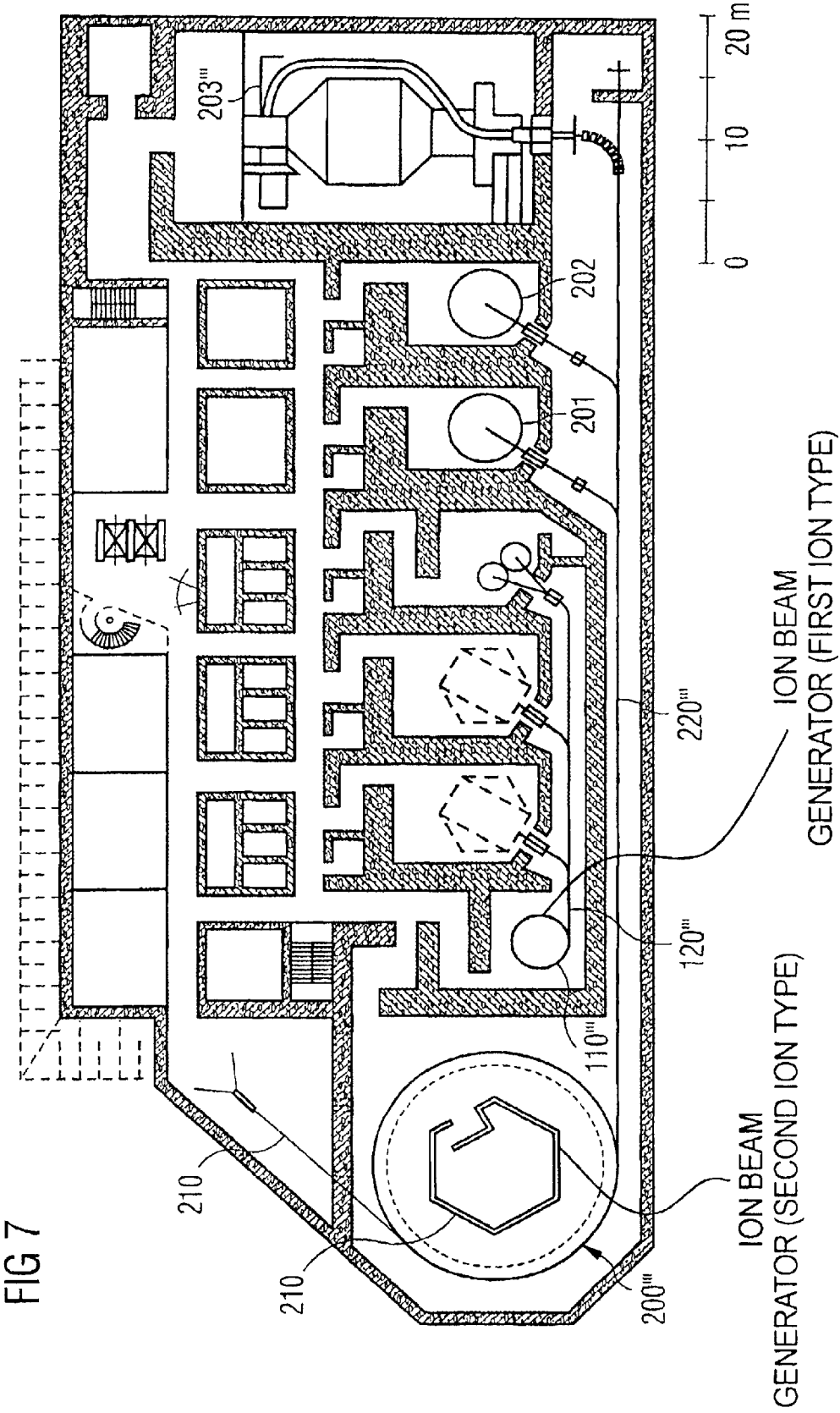
FIG. 7 is a floor plan of a further ion beam facility in accordance with the inventive method having first and second ion beam systems.

As a further exemplary embodiment of the invention, FIG. 7 shows an ion beam facility wherein a first ion beam system 100''' for light ions that essentially corresponds to the first ion beam system 100 is operated in parallel with a second ion beam system 200''' for heavy ions. The ion beam system 200''' has the ion beam generator 210, an ion transport line 220''' as well as irradiation stations 201, 202 and 203'''. The irradiation station 203''', corresponding to the irradiation stations 101 and 102, is fashioned with a rotatable ion beam guidance mechanism and dimensioning for the heavy ions. A compact overall structure of the ion beam facility results due to the parallel guidance of the two ion transport lines 220''' and 120''' at both sides of a radiation-blocking wall'''.

In another exemplary embodiment the ion beam facility of FIG. 7 can proceed from an expansion of the ion beam facility described in FIG. 2, with the above-described advantages. Likewise, of course, the ion beam facilities described in FIGS. 5 and 6 need not necessarily result from the described expansion but can be established in this way from the outset. Due to the parallel guidance of the ion transport lines of the two ion beam systems, simple refitting possibilities of radiation stations that were described above continue to be available for either of the other ion beam systems or for mixed operation.

Although modifications and changes may be suggested by those skilled in the art, it is the intention of the inventors to embody within the patent warranted hereon all changes and modifications as reasonably and properly come within the scope of their contribution to the art.

We claim as our invention:

1. An ion beam facility comprising:
   a first ion beam system for a first ion type having at least two first irradiation stations, a first ion beam generator, a first ion transport line comprising at least one first ion beam switch for communicating said first ion beam generator with one of said first irradiation stations via said first ion transport line;
   a building in which said first ion beam system is disposed, said building having a building wall with a first side along which said first ion transport line is conducted; and
   said wall having an opening therein which is closed and which is prepared for subsequent opening to allow communication of one of said first irradiation stations with a second ion beam system for a second ion type via a subsequently-installable second ion transport line disposed at a second side of said wall, opposite to said first side.

2. An ion beam facility as claimed in claim 1 wherein said building wall is an outside wall of said building.

3. An ion beam facility as claimed in claim 1 wherein said second ion transport line is subsequently installable parallel to said first ion transport line.

4. An ion beam facility as claimed in claim 1 wherein said wall has a removable facing covering said openings.

5. An ion beam facility as claimed in claim 1 wherein said openings are scored in said wall.

6. An ion beam facility as claimed in claim 1 wherein said wall is a radiation-blocking wall for said first and second types of radiation.

7. An ion beam facility as claimed in claim 1 wherein said wall is comprised of concrete and has a thickness of several meters.

8. An ion beam facility as claimed in claim 1 wherein ions of said first ion type are lighter than ions of said second ion type.

9. An ion beam facility as claimed in claim 1 wherein said first ion beam generator generates hydrogen ions, as said ions of said first ion type.

10. An ion beam facility as claimed in claim 1 wherein said first ion transport line proceeds substantially along a straight line.

11. An ion beam facility as claimed in claim 10 wherein said building is adapted to contain second irradiation stations for said second ion beam system following said first irradiation stations along said first and second ion transport lines.

12. An ion beam facility as claimed in claim 11 wherein said building is adapted to contain a second ion beam generator, or said second ion beam system, next to said first ion beam generator.

13. An ion beam facility as claimed in claim 1 wherein said building comprises a plurality of rooms respectively containing said first irradiation stations, each of said rooms having a ceiling, and the ceilings of the respective rooms being substantially at ground level.

14. An ion beam facility as claimed in claim 1 wherein at least one of said first irradiation stations produces an output of ions of said first ion type from said first ion transport line in a rigidly prescribed direction.

15. An ion beam facility as claimed in claim 1 wherein at least one of said first irradiation stations comprises a rotatable ion beam guidance mechanism in communication with said first ion transport line, allowing an output of ions of said first ion type in selected directions that are rotatable around at least one axis.

16. An ion beam facility comprising:
   a first ion beam system for a first ion type having at least two first irradiation stations, a first ion beam generator, a first ion transport line comprising at least one first ion beam switch for communicating said first ion beam generator with one of said first irradiation stations via said first ion transport line;
   a building in which said first ion beam system is disposed, said building having a building wall with a first side along which said first ion transport line is conducted; and
   said building being adapted to reserve space for at least one subsequently installable second ion transport line of a second ion beam system for a second ion type at a second side of said wall, opposite to said first side.

17. An ion beam facility as claimed in claim 16 wherein said building wall is an outside wall of said building.

18. An ion beam facility as claimed in claim 16 wherein said second ion transport line is subsequently installable parallel to said first ion transport line.

19. An ion beam facility as claimed in claim 16 wherein said wall has a removable facing covering said openings.

20. An ion beam facility as claimed in claim 16 wherein said openings are scored in said wall.

21. An ion beam facility as claimed in claim 16 wherein said wall is a radiation-blocking wall for said first and second types of radiation.

22. An ion beam facility as claimed in claim 16 wherein said wall is comprised of concrete and has a thickness of several meters.

23. An ion beam facility as claimed in claim 16 wherein ions of said first ion type are lighter than ions of said second ion type.

24. An ion beam facility as claimed in claim 16 wherein said first ion beam generator generates hydrogen ions, as said ions of said first ion type.

25. An ion beam facility as claimed in claim 16 wherein said first ion transport line proceeds substantially along a straight line.

26. An ion beam facility as claimed in claim 25 wherein said building is adapted to contain second irradiation stations for said second ion beam system following said first irradiation stations along said first and second ion transport lines.

27. An ion beam facility as claimed in claim 26 wherein said building is adapted to contain a second ion beam generator, or said second ion beam system, next to said first ion beam generator.

28. An ion beam facility as claimed in claim 16 wherein said building comprises a plurality of rooms respectively containing said first irradiation stations, each of said rooms having a ceiling, and the ceilings of the respective rooms being substantially at ground level.

29. An ion beam facility as claimed in claim 16 wherein at least one of said first irradiation stations produces an output of ions of said first ion type from said first ion transport line in a rigidly prescribed direction.

30. An ion beam facility as claimed in claim 16 wherein at least one of said first irradiation stations comprises a rotatable ion beam guidance mechanism in communication with said first ion transport line, allowing an output of ions of said first ion type in selected directions that are rotatable around at least one axis.

31. An ion beam facility comprising:
   a first ion beam system for a first ion type comprising at least two first irradiation stations, a first ion beam generator, and a first ion transport line comprising at least one first ion beam switch for communicating said first ion beam generator with one of said first irradiation stations;
   a second ion beam system for a second ion type having a second ion beam generator and a second ion transport line; and
   a switching arrangement for selectively communicating at least one of said first irradiation stations with said second ion beam generator via said second ion transport line for operating said at least one of said first irradiation stations as a part of said second ion beam system.

32. An ion beam facility as claimed in claim 31 wherein said first and second ion transport lines are disposed substantially parallel with each other.

33. An ion beam facility as claimed in claim 31 wherein said first ion beam generator generates ions of said first ion type that are lighter than ions of said second ion type generated by said second ion generator.

34. An ion beam facility as claimed in claim 31 wherein said first ion beam generator generates hydrogen ions, as ions of said first ion type.

35. An ion beam facility as claimed in claim 31 wherein said second ion generator generates carbon ions, as said ions of said second ion type.

36. An ion beam facility as claimed in claim 31 wherein said second ion beam system comprises at least one second irradiation station disposed in said building and communicating with said second ion transport line.

37. An ion beam facility as claimed in claim 36 wherein said at least one second radiation station is disposed following said at least two first irradiation stations in a direction of said first and second ion transport lines.

38. An ion beam facility as claimed in claim 37 wherein said building comprises rooms disposed next to each other respectively containing said ion beam generator and said second ion beam generator.

39. An ion beam facility as claimed in claim 31 wherein at least one of said first irradiation stations produces an output of ions of said first ion type from said first ion transport line in a rigidly prescribed direction.

40. An ion beam facility as claimed in claim 31 wherein at least one of said first irradiation stations comprises a rotatable ion beam guidance mechanism in communication with said first ion transport line, allowing an output of ions of said first ion type in selected directions that are rotatable around at least one axis.

41. An ion beam facility comprising:
a first ion beam system for a first ion type, having at least two first irradiation stations, a first ion beam generator, and a first ion transport line comprising at least one first ion beam switch for communicating said first ion beam generator with at least one of said first irradiation stations; and
a second ion beam system for a second ion type, having a second ion beam generator and a second ion transport line communicating with said second ion generator, said second ion transport line proceeding substantially parallel to said first ion transport line.

42. An ion beam facility as claimed in claim 41 wherein said first ion beam generator generates ions of said first ion type that are lighter than ions of said second ion type generated by said second ion generator.

43. An ion beam facility as claimed in claim 41 wherein said first ion beam generator generates hydrogen ions, as ions of said first ion type.

44. An ion beam facility as claimed in claim 41 wherein said second ion generator generates carbon ions, as said ions of said second ion type.

45. An ion beam facility as claimed in claim 41 wherein said second ion beam system comprises at least one second irradiation station disposed in said building and communicating with said second ion transport line.

46. An ion beam facility as claimed in claim 45 wherein said at least one second radiation station is disposed following said at least two first irradiation stations in a direction of said first and second ion transport lines.

47. An ion beam facility as claimed in claim 46 wherein said building comprises rooms disposed next to each other respectively containing said ion beam generator and said second ion beam generator.

48. An ion beam facility as claimed in claim 41 wherein at least one of said first irradiation stations produces an output of ions of said first ion type from said first ion transport line in a rigidly prescribed direction.

49. An ion beam facility as claimed in claim 41 wherein at least one of said first irradiation stations comprises a rotatable ion beam guidance mechanism in communication with said first ion transport line, allowing an output of ions of said first ion type in selected directions that are rotatable around at least one axis.

50. A method for constructing an ion beam facility to allow for future expansion, comprising the steps of:
constructing a building comprising a plurality of rooms including a first room and a second room;
disposing a first ion beam generator of a first ion beam system for a first ion type in said first room;
disposing a first irradiation station of said first ion beam system in said second room;
at a first side of a wall of said building, constructing a first ion transport line between said first room and said second room, allowing ions of said first ion type to proceed from said first ion beam generator in said first room to said first irradiation station in said second room via said first ion transport line; and
providing at least one closed opening in said wall prepared for subsequent opening of said opening to allow ions of a second ion type, generated by a subsequently installed second ion beam generator of a second ion beam system, to proceed from said second ion beam generator via a second ion transport line, disposed at a second side of said wall, opposite to said first side, to said first irradiation station.

51. A method as claimed in claim 50 comprising opening said openings in said wall and installing said second ion beam system with said second ion transport line at said second side of said wall.

52. A method as claimed in claim 51 comprising constructing said second ion transport line substantially parallel to said first ion transport line.

53. A method as claimed in claim 51 comprising providing a switching arrangement allowing selective communication between said first irradiation station and one of said first ion transport line and said second ion transport line at a time, for selectively operating said first irradiation station with ions of said first ion type or ions of said second ion type.

54. A method as claimed in claim 51 comprising generating ions of said first ion type with said first ion generator that are lighter than ions of said second ion type generated by said second ion generator.

55. A method as claimed in claim 54 comprising generating hydrogen ions, as ions of said first ion type, with said first ion beam generator.

56. A method as claimed in claim 54 comprising generating carbon ions, as said ions of said second ion type, with said second ion generator.

57. A method as claimed in claim 51 wherein the step of installing said second ion beam system comprises constructing a third room of said building next to said first room, and disposing said second ion beam generator in said second room.

58. A method as claimed in claim 57 wherein the step of installing said second ion beam system further comprises constructing a fourth room in said building and disposing a second irradiation station in said fourth room, said second ion transport line being disposed between said third room and said fourth room, allowing said ions of said second ion type to proceed from said second ion beam generator in said third room to said second irradiation station in said fourth room.

59. A method as claimed in claim 50 comprising producing an output of ions of said first ion type at said first irradiation station from said ion transport line in a rigidly prescribed direction.

60. A method as claimed in claim 50 comprising producing an output of ions of said first ion type at said first irradiation station from said first ion transport line in selected directions that are rotatable around at least one axis.

61. A method as claimed in claim 50 comprising constructing said wall as a radiation-blocking wall for ions of said first and second types.

* * * * *